US011439849B2

(12) United States Patent
Pollock et al.

(10) Patent No.: US 11,439,849 B2
(45) Date of Patent: Sep. 13, 2022

(54) METHOD OF MARKERLESS MEASUREMENT AND CALCULATION FOR PERSONALIZED AND REPRODUCIBLE BREATH HOLDS FOR RADIATION THERAPY AND MEDICAL IMAGING

(71) Applicant: Opus Medical Pty Ltd, Eveleigh (AU)

(72) Inventors: Sean Pollock, Redfern (AU); Paul J. Keall, Greenwich (AU)

(73) Assignee: Opus Medical Pty Ltd

( * ) Notice: Subject to any disclaimer, the term of this patent is extended or adjusted under 35 U.S.C. 154(b) by 591 days.

(21) Appl. No.: 16/485,930

(22) PCT Filed: Feb. 13, 2018

(86) PCT No.: PCT/EP2018/053592
§ 371 (c)(1),
(2) Date: Aug. 14, 2019

(87) PCT Pub. No.: WO2018/149837
PCT Pub. Date: Aug. 23, 2018

(65) Prior Publication Data
US 2020/0038690 A1    Feb. 6, 2020

Related U.S. Application Data

(60) Provisional application No. 62/464,053, filed on Feb. 27, 2017, provisional application No. 62/464,074, (Continued)

(51) Int. Cl.
*A61B 6/00*     (2006.01)
*A61N 5/10*     (2006.01)
(Continued)

(52) U.S. Cl.
CPC ............ *A61N 5/1068* (2013.01); *A61B 6/035* (2013.01); *A61B 6/0407* (2013.01); *A61B 6/08* (2013.01); *A61N 2005/1074* (2013.01)

(58) Field of Classification Search
CPC ..................... A61N 2005/1074; A61N 5/1068
See application file for complete search history.

(56) References Cited

U.S. PATENT DOCUMENTS 6,690,965 B1   2/2004   Riaziat et al.
7,575,554 B2   8/2009   Onishi
(Continued)

*Primary Examiner* — Dani Fox
(74) *Attorney, Agent, or Firm* — Lumen Patent Firm

(57) ABSTRACT

A method of customized breathing maneuver guidance during radiotherapy treatment by configuring to a treatment couch an augmented reality system that includes a mounting assembly, a position measurement module to measure a distance from a fixed position to a patient anatomic region during a breathing cycle, and a breath monitoring and instruction screen viewable by the patient disposed proximal to the fixed position, where the patient monitors and controls a state of their breathing cycle in real time from breath state information displayed on the instruction screen, and determining the anatomic region for monitoring to measure the distance from the fixed position, determining a patient-customized breath hold amplitude by measuring a distance between a baseline exhale position a maximum inhale position, and entering breath hold amplitude data to a computer for subsequent breath hold guidance regardless of the treatment couch model setup and patient weight variations.

8 Claims, 6 Drawing Sheets

Related U.S. Application Data filed on Feb. 27, 2017, provisional application No. 62/458,978, filed on Feb. 14, 2017.

(51) Int. Cl.
*A61B 6/03* (2006.01)
*A61B 6/04* (2006.01)
*A61B 6/08* (2006.01)

(56) References Cited

U.S. PATENT DOCUMENTS

| | | |
|---|---|---|
| 7,783,335 B2 | 8/2010 | Le Corre |
| 2003/0188757 A1 | 10/2003 | Yanof |
| 2015/0306340 A1* | 10/2015 | Giap ............... A61B 6/46 |
| | | 600/301 |

\* cited by examiner

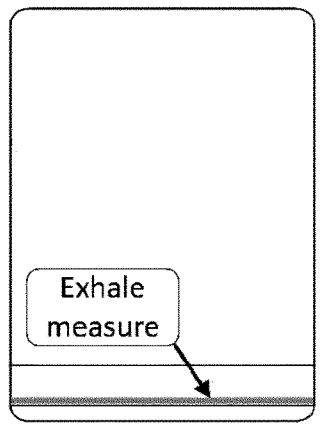
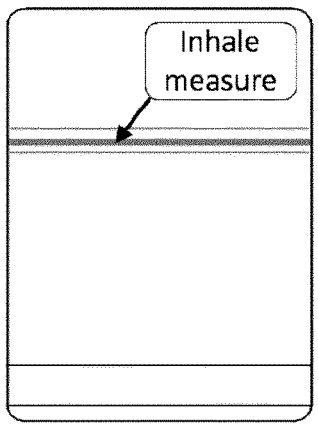
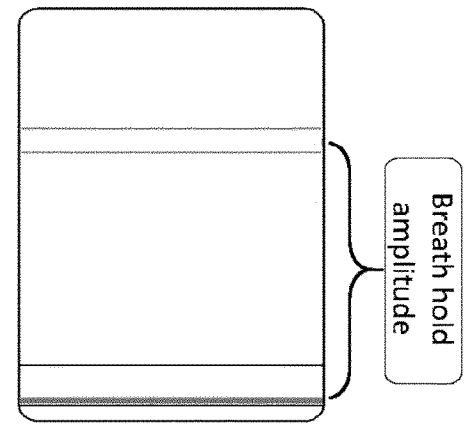
*FIG. 3A*   *FIG. 3B*   *FIG. 3C*
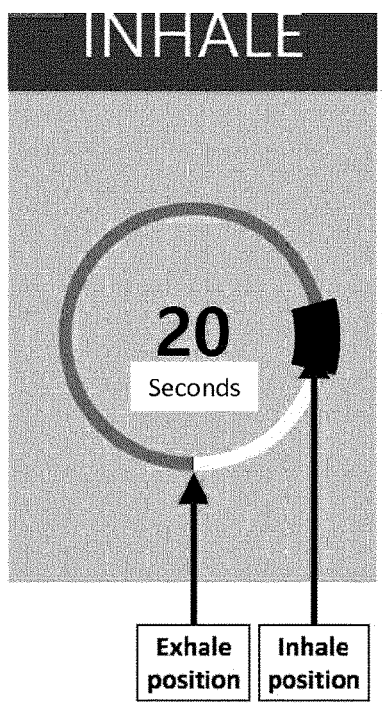
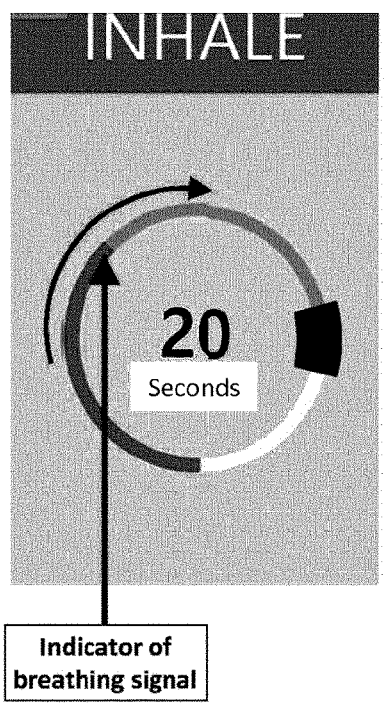
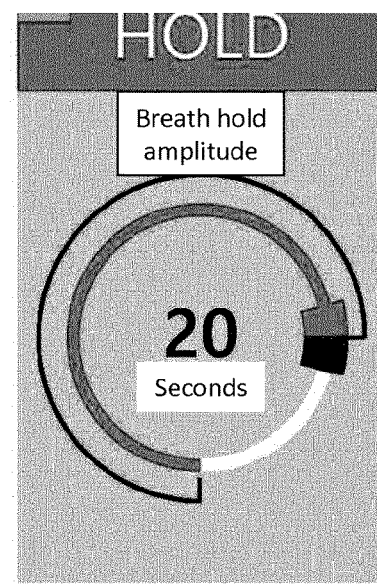
*FIG. 3D*   *FIG. 3E*   *FIG. 3F*

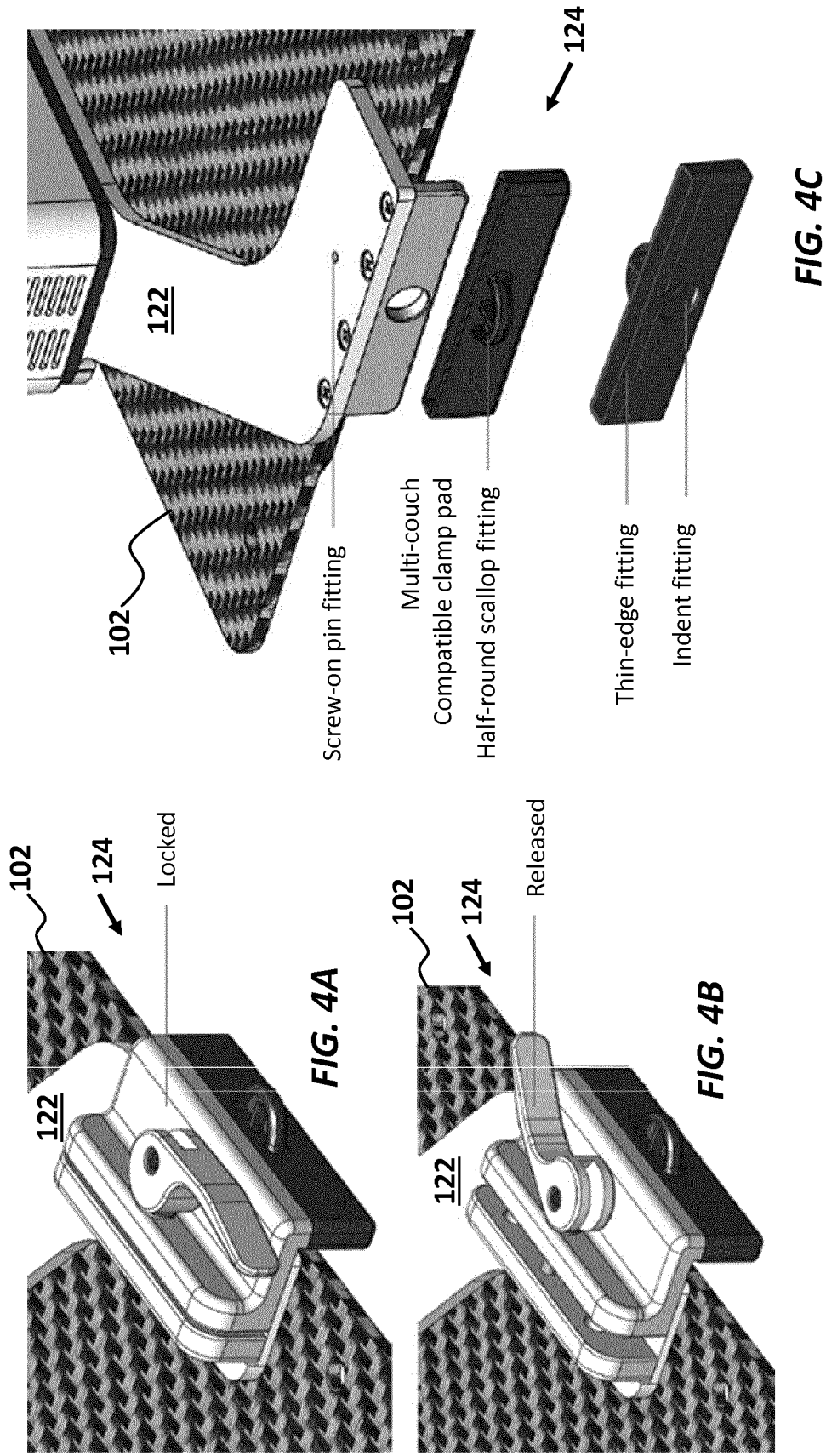

METHOD OF MARKERLESS MEASUREMENT AND CALCULATION FOR PERSONALIZED AND REPRODUCIBLE BREATH HOLDS FOR RADIATION THERAPY AND MEDICAL IMAGING

CROSS-REFERENCE TO RELATED APPLICATIONS

This application is a 371 of PCT application PCT/EP2018/053592 filed Feb. 13, 2018. PCT application PCT/EP2018/053592 claims the benefit of U.S. Provisional applications 62/464,053 filed Feb. 27, 2017, 62/458,978 filed Feb. 14, 2017 and 62/464,074 filed Feb. 27, 2017.

FIELD OF THE INVENTION

The present invention relates generally to radiation therapy. More particularly, the invention relates to a method of markerless breath hold for radiation therapy and imaging.

BACKGROUND OF THE INVENTION

Breath hold breathing maneuvers, particularly deep inhalation breath holds, are a treatment technique for thoracic and abdominal cancer patients in radiotherapy in addition to non-cancer patients during interventional cardiology and radiology procedures. During such breath hold maneuvers the patient holds their breath to facilitate stationary anatomic and tumor position in addition increasing the lung volume and decreasing the amount of heart in the radiation field to reduce short and longterm side effects of radiotherapy.

Current breath hold maneuvers are performed using:
(1) Uncomfortable, invasive devices that use spirometry and often increase the overall procedure workflow time,
(2) Verbal instruction provided by the treatment staff, for which patient compliance and procedure reproducibility is not ideal,
(3) Respiratory monitors and displays that show a breathing signal measured by a respiratory monitor, with much of the workflow involved requiring manual input at each step. Additionally, this method often requires the use of external motion surrogates, the reliability of which as indicators for the desired anatomic motion has yielded mixed experimental results.

A key component of such medical procedures is that the exact same breath hold level needs to be repeated by the patient multiple times, often across multiple days of treatment. None of the procedures outlined in points (1)-(3) incorporate an automated method to provide customized breathing maneuver guidance in such a way that it can be replicated multiple times across multiple days regardless of variations in patient size and position. Manually performing these steps, as done in the methods outlined in points (1)-(3), increases the risk of user error, increases the time needed to perform such procedures, and compromises patient compliance.

Patient coaching and monitoring by the treatment staff is limited by cameras not designed for close patient views, unclear audio, the gantry getting in the way of the camera, the inability to monitor the breath hold position during CT scanning—an integral part of the radiotherapy process crucial to overall treatment accuracy—and also the patient is not monitoring their own breathing.

Additionally, in radiology and radiation oncology numerous devices are used to physically stabilize patient position and other purposes such as respiratory sensors and respiratory control. Such patient positioning methods (e.g. body-frames, arm-stirrups) lock into notches on the sides of the imaging/treatment couches to (i) keep the patient firmly in position, and (ii) ensure reproducibility of the patient setup by noting the notched position of the couch notches.

However, different vendors have different designs of these couch notches to lock equipment into position, and as such, there is not a "one size fits all" solution, each of the vendor's couches requires vendor-specific equipment to lock into.

There is currently no universal platform-agnostic couch-mounting mechanism for either respiratory sensors or patient positioning equipment. In radiology and radiation oncology numerous devices are used to physically stabilize patient position and other purposes such as respiratory sensors and respiratory control. Equipment compatibility across a range of vendors' platforms would greatly improve the efficiency and convenience of procedures in departments that have multiple vendors' imaging and treatment machines. Further to this, such a solution would also reduce the footprint of equipment needed in a department, negating the need for multiple pieces of the same equipment for different vendors' platforms.

Furthermore, given the variety of setup variations that occur across these procedures, the ability to (i) adjust to a variety different positions and (ii) record these positions to assist in setup reproducibility are highly advantageous, but not provided by existing medical devices.

Breath hold radiotherapy, particularly deep inspiration breath hold (DIBH), is a treatment technique for breast cancer patients (and other cancer types, such as lung) in which the patient holds her (or his) breath to increase the lung volume and decrease the amount of heart in the radiation field to reduce short and long term side effects of radiotherapy.

SUMMARY OF THE INVENTION

To address the needs in the art, a method of customized breathing maneuver guidance during radiotherapy treatment is provided that includes configuring an augmented reality system to a treatment couch, where the augmented reality system includes a mounting assembly, a position measurement module configured to measure a distance from a fixed position to an anatomic region of a patient during a patient breathing cycle, and a patient breath monitoring and instruction screen that is viewable by the patient and is disposed proximal to the fixed position, where the patient monitors and controls a state of their breathing cycle in real time according to breath state information displayed on the breath monitoring and instruction screen, using the augmented reality system to determine the anatomic region for monitoring and to measure the distance from the fixed position, using the augmented reality system to determine a patient-customized breath hold amplitude of the anatomic region of the patient by measuring a distance between a baseline exhale position of the anatomical region of the patient and a maximum inhale position of the anatomical region of the patient using the position measurement module and the monitoring screen, and entering patient-customized breath hold amplitude data to a computer and computer storage medium, where the patient-customized breath hold amplitude data includes the anatomic region, the breath hold amplitude position, and the fixed position, where the patient-customized breath hold amplitude data is used for subsequent breath hold guidance regardless of the treatment couch model setup and patient weight variations.

In one aspect of the invention, the position measurement module includes an IR distance position or a camera.

In another aspect of the invention, the patient breath monitoring screen displays data can include real-time breathing position data, real-time exhale position data, real-time inhale position data, real-time breath hold position data, stored breathing position data, stored exhale position data, or stored inhale position data, stored breath hold position data.

In a further aspect of the invention, the anatomic region comprises a topographical feature that is natural to the patient, or a marking incorporated to the patient.

According to one aspect of the invention, the augmented reality system mounting assembly includes a base assembly having base position index markings, a CPU assembly, an elbow assembly having elbow position index markings, the sensor assembly having sensor position index markings, a position measurement mount assembly having position measurement module position index markings, and a breath monitoring screen mount assembly, where the base assembly comprises clamping elements disposed to frictionally clamp the base assembly to the treatment couch, where couch model data and data of all the position markings is entered to the computer and computer storage medium. In one aspect, the clamping elements are configured to affix the base assembly to a couch having a treatment couch edge shape that can include a concave groove, a convex bulb, holes, or holes with a different radius. In a further aspect, the clamping elements are configured to affix the base assembly to different the couches having different widths, different thicknesses, or different curvatures.

In another aspect, the patient-customized breath hold amplitude data is reproduced by positioning the augmented reality system mounting assembly using markings on the mounting assembly, or using positioning motors operated by the computer using the position sensor and the stored patient-customized breath hold amplitude data.

In a further aspect of the invention, \the augmented reality system is does not obstruct a path of a radiotherapy treatment beam, or a path of a CT imaging device when connected to the treatment couch.

BRIEF DESCRIPTION OF THE DRAWINGS

FIGS. 3A-3F show exemplary graphical interfaces visible to the treatment staff and patient indicating the (3A, 3D) exhale measure, (3B, 3E) inhale measure, and (3C, 3F) calculated breath hold amplitude, according to different embodiments of the invention.

FIGS. 4A-4C show the clamping elements disposed to frictionally clamp the base assembly clamping elements disposed to frictionally clamp the base assembly to the treatment couch to the treatment couch clamping elements disposed to frictionally clamp the base assembly to the treatment couch, according to one embodiments of the invention.

DETAILED DESCRIPTION

To address the limitations of current patient breathing maneuver methods, a markerless method of measurement and calculation is provided for personalized and reproducible breath holds for radiation therapy and medical imaging procedures. This method operates under the following Principles:
  (1) Utilizing augmented reality to determine the desired patient anatomy to monitor.
  (2) Measuring the distance between baseline exhale position and maximum inhale position to determine the patient-customized breath hold amplitude.
  (3) Loading the patient-customized (i) anatomic position to monitor, and (ii) breath hold amplitude for subsequent breath hold maneuvers regardless of setup and patient weight variations.

According to one aspect of the invention, the patients find it easier to follow the therapy and therapist's instructions and technique when presented with a visual guide based on their own anatomy. Further, treatment staff find it easy to observe and monitor as it requires minimal intervention. The device is introduced into the existing workflow and improves the overall standard of care by engaging the patient closely with their treatment. The patients are also in control of their treatment which is empowering.

The system used for biofeedback with augmented reality for breath hold radiotherapy includes an imaging device, a screen and a computer to process and build augmented reality images in real time and also enable remote communication with treatment team, and between the treatment team and the patient.

Figures 1A, 1B:
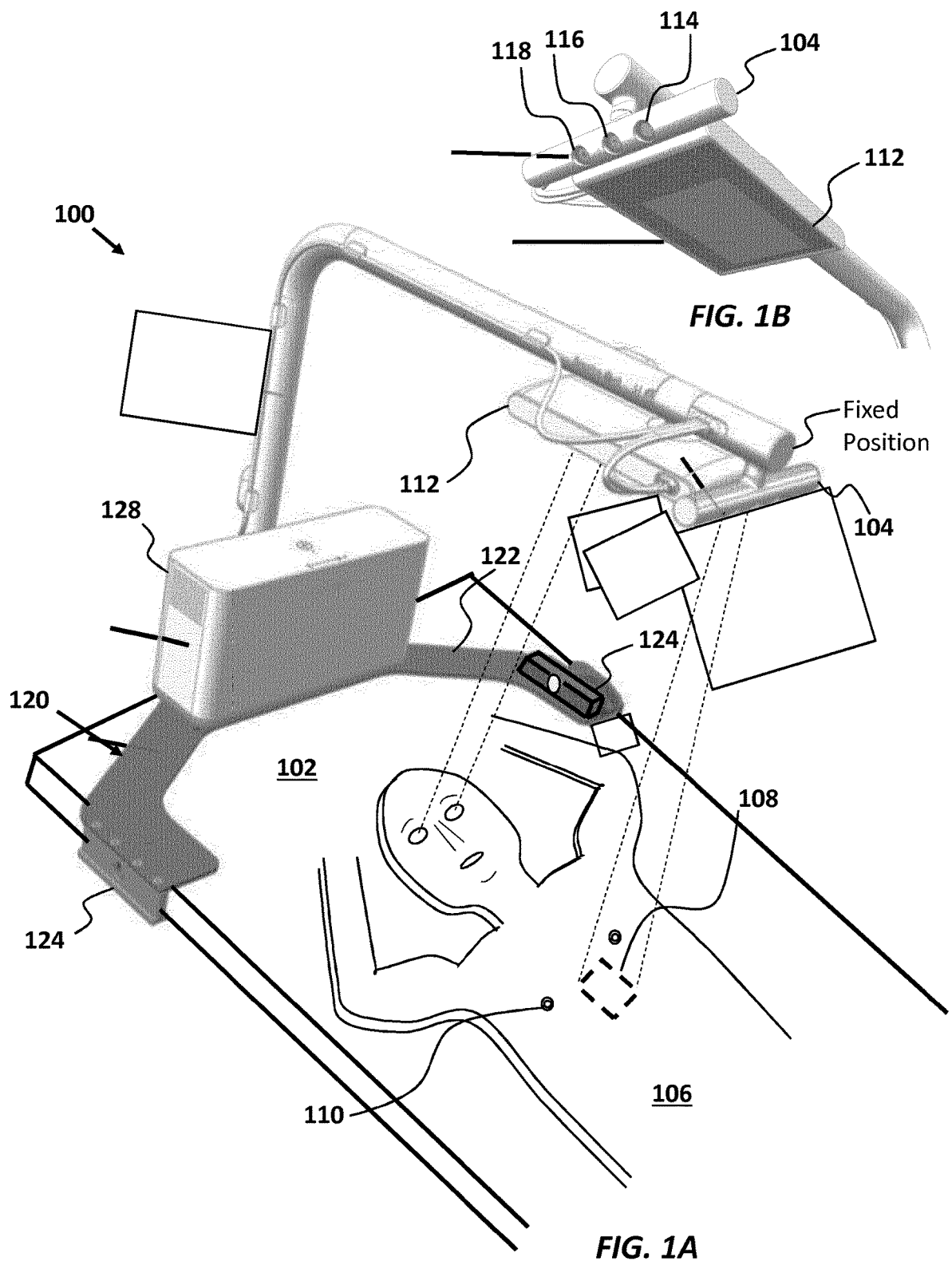
FIG. 1A shows an augmented reality system configured to a treatment couch with the position measurement module positioned above the patient, according to one embodiment of the invention.
FIG. 1B shows perspective view of the position measuring module, according to one embodiment of the invention.
Figure 2A:
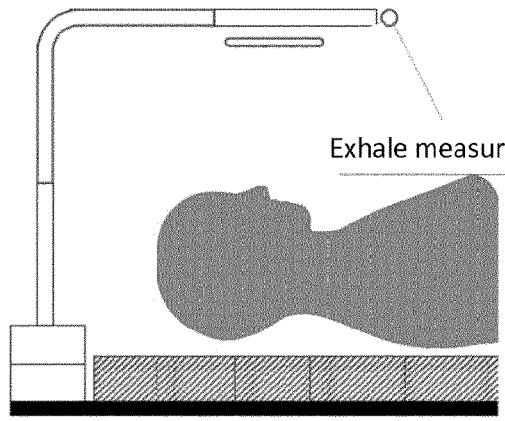
FIGS. 2A-2D show schematic of drawings of the customized breath hold amplitude, where (2A) shows an exhale position measurement value, (2B) an inhale position measurement value, where the breath hold amplitude is determined based on the change between exhale and inhale measurements, and further shown is the same patient and their determined breath hold amplitude at (2C) one time, and (2D) a later time where they have experienced weight loss and variations in setup position, according to one embodiment of the invention.
Figure 2B:
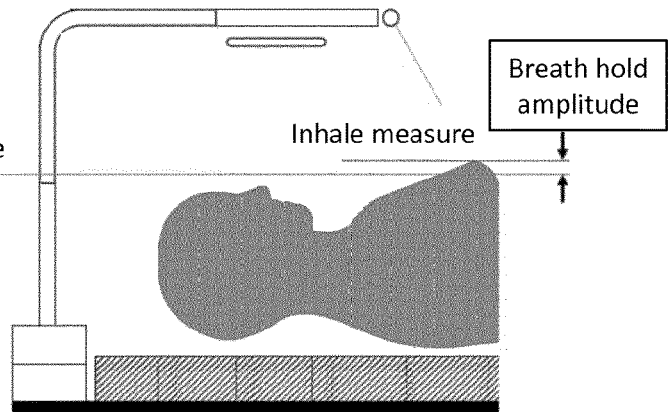
Figure 2C:
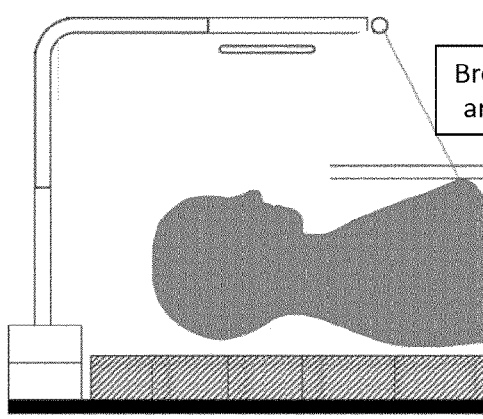
Figure 2D:
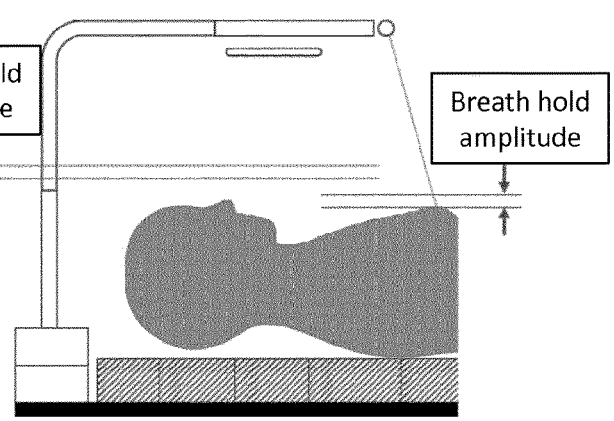

One embodiment of the current invention is shown in FIG. 1A, where an augmented reality system 100 is configured to a treatment couch 102. A respiratory position measurement module 104 is positioned above the patient 106 and is configured to monitor the amplitude of the patient's respiratory-induced chest motion. FIG. 1B shows perspective view of the position measuring module 104, where shown is the patient breath monitoring and instruction screen 112, a distance measurement emitter 114, for example an IR beam, an emitter detector 116, and a camera 118.

In one embodiment of the invention, the treatment staff utilize a camera within the position measuring module 104 the augmented reality system to obtain an optical view of the anatomic region 108 to monitor for respiratory amplitude. The anatomic region 108 to monitor (indicated by the dashed rectangle in FIG. 1A) can be adjusted in terms of position and size by the treatment staff to ensure the desired anatomic region 108 to measure is achieved. The use of tattoos and anatomic landmarks 110 is common practice in these medical procedures and can be used, and aligning the anatomical region 108 to monitor with these tattoos and anatomic landmarks 110 will ensure reproducibility of patient respiratory amplitude across multiple days of breath hold procedures.

Further shown in FIG. 1A, the augmented reality system 100 includes a mounting assembly 120 having a mounting base 122, that has a universal clamping mechanism 124 disposed to frictionally clamp the mounting base 122 to any treatment couch 102 geometry commonly known in the art.

The breath hold amplitude is saved for each patient to be replicated on subsequent imaging and radiotherapy procedures, this is determined through loading the patient-customized anatomic position to monitor, and breath hold amplitude for subsequent breath hold maneuvers regardless of setup and patient weight variation. By having a fixed breath hold amplitude measurement and maintaining consistent monitoring of patient anatomy through this process and by measuring the distance between the baseline exhale position and the maximum inhale position, the patient-customized breath hold amplitude is determined.

FIGS. 2A-2D show schematic of drawings of the customized breath hold amplitude, where (2A) shows an exhale position measurement value, (2B) an inhale position measurement value. Here, the breath hold amplitude is determined based on the change between exhale and inhale measurements, and further shown is the same patient and their determined breath hold amplitude at (2C) one time, and (2D) a later time where they have experienced weight loss and variations in setup position. In this embodiment, the augmented reality system 100 position measurement module 104 and software account for these changes such that the patient performs the same breath hold based on their breath hold amplitude. By maintaining consistent measurements of patient anatomy and breath hold amplitudes with the graphical feedback, the patient will be performing the same breath hold for each radiation therapy and medical imaging procedure regardless of patient weight changes and setup variations that occur between such procedures.

Turning now to universal clamping mechanism 124 configured to ensure platform-agnostic compatibility of equipment locking onto a wide variety of vendors' imaging/treatment couches. FIGS. 4A-4C show the clamping elements 124 disposed to frictionally clamp the base assembly clamping elements disposed to frictionally clamp the base assembly to the treatment couch 102 to the treatment couch clamping elements disposed to frictionally clamp the base assembly to the treatment couch 102. According to one embodiment, the clamping element 124 is positioned over the edge of either side of the couch 102, the in-built fittings fit into/over a wide range of vendors' couch notches. Pressing the locking lever into the 'locked' position reduces the width of the clamping element, fastening it securing into place in the desired notched couch position. In one aspect, the clamping elements 124 are configured to affix the base assembly 122 to a couch 102 having a treatment couch edge shape that can include many shapes such as a concave groove, a convex bulb, holes, or holes with a different radius. In a further aspect, the clamping elements CPU assembly 124 are configured to affix the base assembly 122 to different the couches 102 having different widths, different thicknesses, or different curvatures. By enabling compatibility across a wide range of vendors' platforms, the clamping element 124 facilitates more convenient equipment setups, reduces the footprint of equipment needed in a radiology or radiation oncology department, and doesn't limit the equipment used to only come from a single vendor.

Figure 5A:
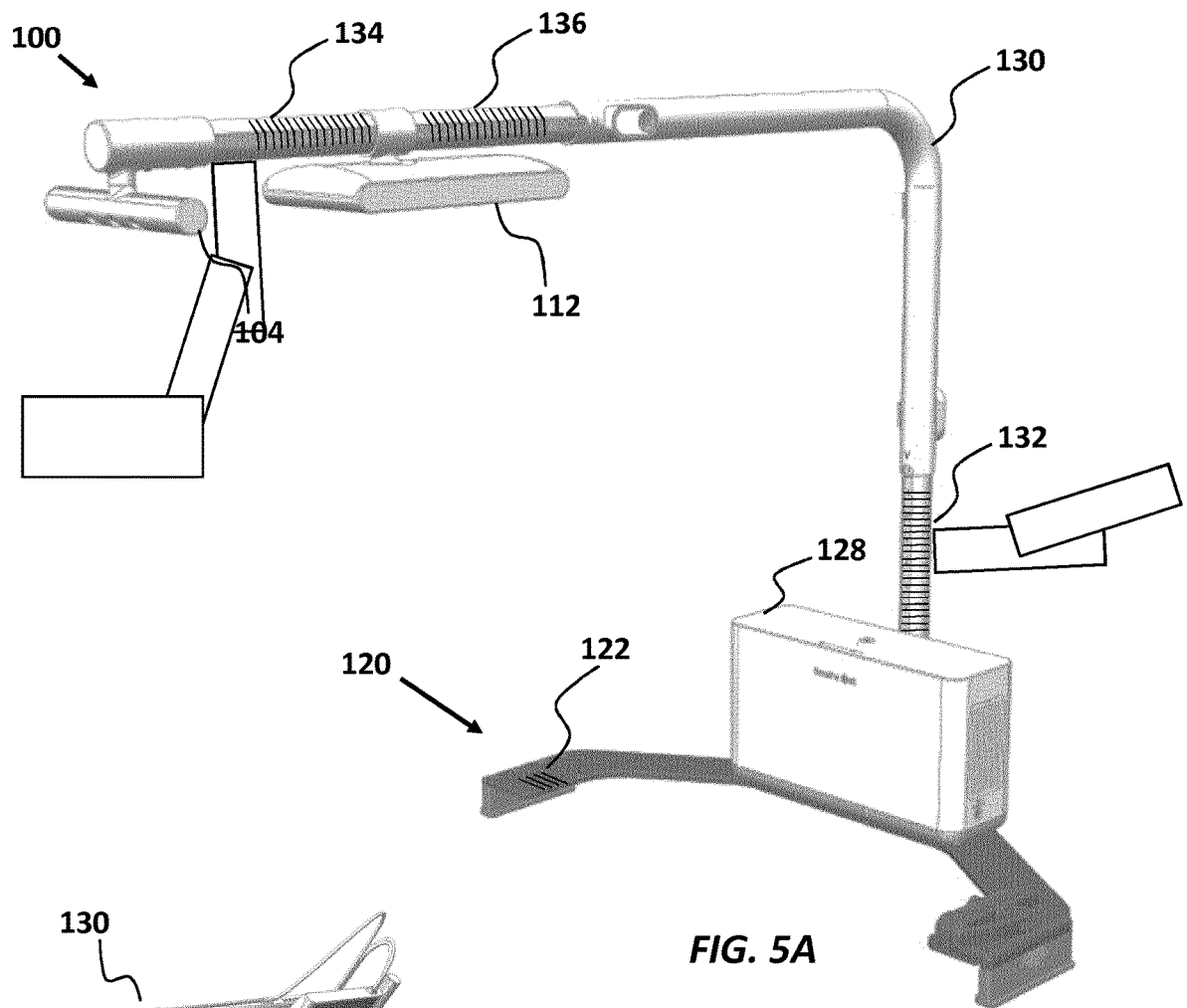
FIGS. 5A-5B show the augmented reality system having index markings on important portions of the mounting assembly, according to one embodiment of the invention.
Figure 5B:
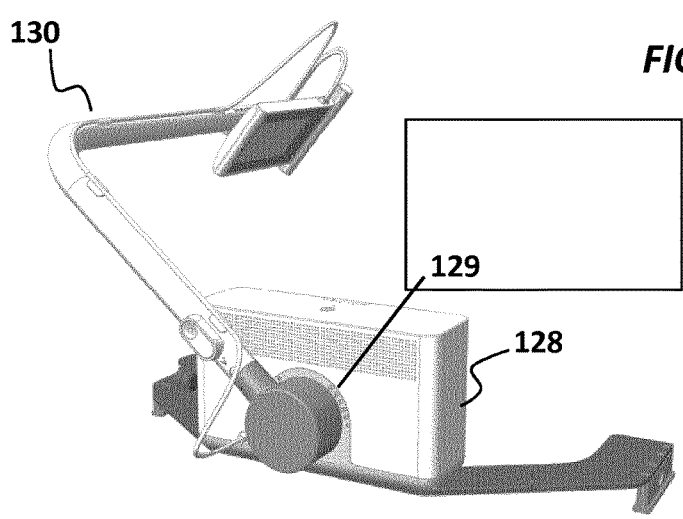

To facilitate the measurement repeatability, FIGS. 5A-5B show one embodiment of the augmented reality system 100 includes index markings on important portions of the mounting assembly 120 having the base assembly 120 having base assembly position index markings 126, a CPU assembly 128 has radial position markings 129, an elbow assembly 130 having elbow position index markings 132, where the CPU assembly 128 has radial position markings 129 for the elbow assembly 130. In FIG. 5A, the respiratory position measurement module 104 is shown having respiratory position measurement module position index markings 134, a patient breath monitoring and instruction screen 112 having position measurement module position index markings 136, where couch model data and data of all the position markings is entered to the computer and computer storage medium (CPU assembly) 128.

Figure 6A:
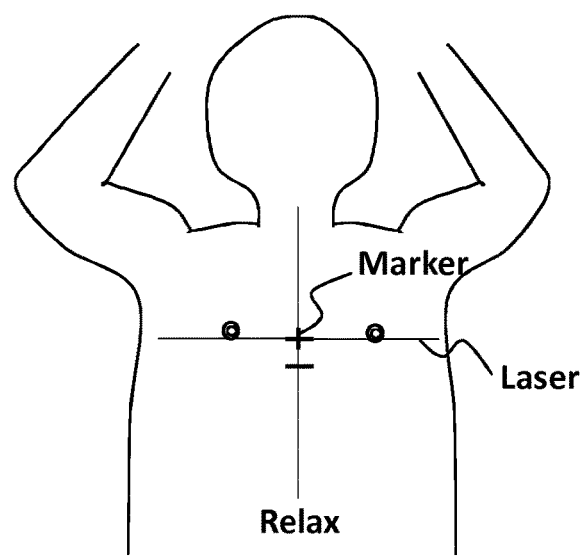
FIGS. 6A-6B show lasers used to determine and measure the change in the chest position without and with breath hold, according to one embodiment of the invention.
Figure 6B:
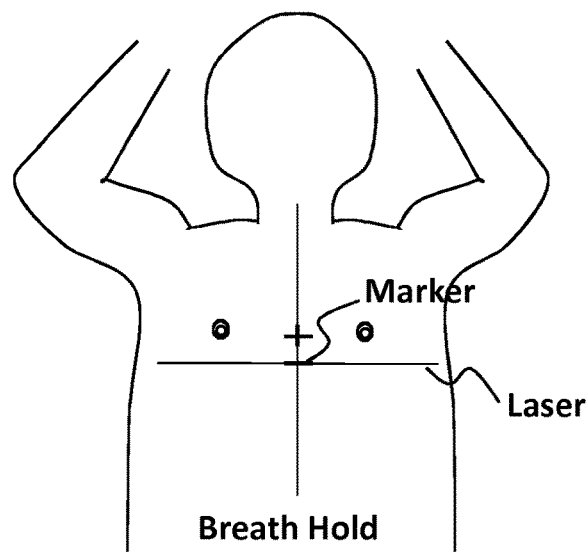

According to one embodiment, the method of operation of biofeedback with augmented reality for breath hold radiotherapy is shown in FIGS. 6A-6B. In current practice, lasers, commonly available in the imaging and treatment rooms in cancer radiotherapy departments, can be used to determine and measure the change in the chest position without and with breath hold (FIGS. 6A-6B). Where lasers are available, the system can still be used without the augmented reality virtual laser, with the patient still being in control of their treatment and able to maintain a consistent breath hold. The positions without breath hold and with a comfortable breath hold can be marked on the patient's skin using permanent or semi-permanent markers. These positions can be viewed by the patient on the patient breath monitoring and instruction screen (not shown), which can be useful for facilitating gross alignment of the augmented reality system 100 and the patient 106 between treatments from one day to the next.

According to other aspects of the invention, audio and visual prompts can be given to the patient, for example, as a lead in to the breath hold to breathe in, breathe out, breathe in and hold, counting the length of the breath hold (up to or down from the desired length). Additional messages, such as to relax, or prepare for a breath hold can also be given.

The patient may be set up to the permanent or semi-permanent marks at the breath hold position. An alternative is to set up the patient to the non-breath hold marks, and then image and treat with the patient in the breath hold state.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method of customized breathing maneuver guidance during radiotherapy treatment, comprising:
   a) configuring an augmented reality system to a treatment couch, wherein said augmented reality system comprises a mounting assembly, a position measurement module configured to measure a distance from a fixed position to an anatomic region of a patient during a patient breathing cycle, and a patient breath monitoring and instruction screen that is viewable by said patient and is disposed proximal to said fixed position, wherein said patient monitors and controls a state of their breathing cycle in real time according to breath state information displayed on said breath monitoring and instruction screen;
   b) using said augmented reality system to determine said anatomic region for monitoring and to measure said distance from said fixed position; and
   c) using said augmented reality system to determine a patient-customized breath hold amplitude of said anatomic region of said patient by measuring a distance between a baseline exhale position of said anatomical region of said patient and a maximum inhale position of said anatomical region of said patient using said position measurement module and said patient breath monitoring and instruction screen;

d) entering patient-customized breath hold amplitude data to a computer and computer storage medium, wherein said patient-customized breath hold amplitude data comprises said anatomic region, said breath hold amplitude position, and said fixed position, wherein said patient-customized breath hold amplitude data is used for subsequent breath hold guidance regardless of said treatment couch model setup and patient weight variations, wherein said patient-customized breath hold amplitude data is reproduced by positioning said augmented reality system mounting assembly using markings on said mounting assembly, or using positioning motors operated by said computer using said position sensor and said stored patient-customized breath hold amplitude data.

2. The method according to claim 1, wherein said position measurement module comprises an IR distance sensor, or a camera.

3. The method according to claim 1, wherein said patient breath monitoring screen displays data selected from the group consisting of real-time breathing position data, real-time exhale position data, real-time inhale position data, real-time breath hold position data, stored breathing position data, stored exhale position data, and stored inhale position data, stored breath hold position data.

4. The method according to claim 1, wherein said anatomic region comprises a topographical feature that is natural to said patient, or a marking incorporated to said patient.

5. The method according to claim 1, wherein said augmented reality system mounting assembly comprises a base assembly having base position index markings, a CPU assembly, an elbow assembly having elbow position index markings, said sensor assembly having sensor position index markings, a position measurement mount assembly having position measurement module position index markings, and a breath monitoring screen mount assembly, wherein said base assembly comprises clamping elements disposed to frictionally clamp said base assembly to said treatment couch, wherein couch model data and data of all said position markings is entered to said computer and computer storage medium.

6. The method according to claim 5, wherein said clamping elements are configured to affix said base assembly to a couch having a treatment couch edge shape selected from the group consisting of concave groove, a convex bulb, holes, and holes with a different radius.

7. The method according to claim 5, wherein said clamping elements are configured to affix said base assembly to different said couches having different widths, different thicknesses, or different curvatures.

8. The method of claim 1, wherein a position of said augmented reality system is does not obstruct a path of a radiotherapy treatment beam, or a path of a CT imaging device.

* * * * *